United States Patent [19]

Said

[11] 4,080,336
[45] Mar. 21, 1978

[54] PROCESS FOR THE PRODUCTION OF 2-CHLORONICOTINIC ACID AMIDE

[75] Inventor: Adel Said, Brig, Switzerland

[73] Assignee: Lonza Ltd., Gampel, Switzerland

[21] Appl. No.: 784,321

[22] Filed: Apr. 4, 1977

[30] Foreign Application Priority Data

Apr. 2, 1976   Switzerland ......................... 4125/76

[51] Int. Cl.$^2$ ........................................... C07D 213/56
[52] U.S. Cl. ...................... 260/295.5 A; 260/295.5 R
[58] Field of Search ................................ 260/295.5 A

[56] References Cited

FOREIGN PATENT DOCUMENTS 80,209   10/1971   Germany ..................... 260/295.5 R

*Primary Examiner*—Alan L. Rotman
*Attorney, Agent, or Firm*—Virgil H. Marsh

[57] ABSTRACT

The process for the production of 2-chloronicotinic acid amide from nicotinic acid-N-oxide, characterized in that 2-chloronicotinic acid chloride is distilled off from the nicotinic acid-N-oxide reaction product and the distilled 2-chloronicotinic acid chloride is allowed to flow into an amine at a temperature of 0° to 60° C. The 2-chloronicotinic acid chloride is ammonlyzed to 2-chloronicotinic acid amide, which precipitates in a crystalline form.

8 Claims, No Drawings

PROCESS FOR THE PRODUCTION OF 2-CHLORONICOTINIC ACID AMIDE

BACKGROUND OF THIS INVENTION

1. Field of This Invention

This invention relates to a process for the production of 2-chloronicotinic acid amide for nicotinic acid-N-oxide.

2. Prior Art

E. Kretzschmer et al., East German Pat. No. 44,132 (1965), teaches that 2-chloronicotinic acid amide prepared from 2-chloronicotinic acid nitrile by partial saponification using an ion exchanger (Wofatit SBW). The yield amounted to 75 percent, related to the 2-chloronicotinic acid nitrile; the product has a melting point of 164° to 165° C. E. Taylor et al., J. Org. Chem., 19, 1633 (1954), teaches that 2-chloronicotinic acid amide can be produced from 2-chloronicotinic acid nitrile, KOH and $H_2O_2$ in ethanol. The yield is 62 percent, related to the 2-nicotinic acid nitrile. The disadvantages of both prior art processes lies with the starting material, which is difficult to obtain (as it is produced from nicotinic acid amide by treatment with $H_2O_2$ and acetic acid, and subsequently with $PCl_5$ and $POCl_3$). The yield of starting nitrile is 40 percent.

BROAD DESCRIPTION OF THIS INVENTION

An object of this invention is to achieve a process for the production of a pure white 2-chloronicotinic acid amide in a good yield and at a relatively small cost. Other objects and advantages of this process are set out herein or are obvious herefrom to one ordinarily skilled in the art.

The objects and advantages of this invention are achieved by the process of this invention.

This invention involves the process of distilling 2-chloronicotinic acid chloride out of the reaction mixture. The reaction mixture normally results from the conversion of nicotinic acid-N-oxide into 2-chloronicotinic acid chloride. The distilled 2-chloronicotinic acid chloride is allowed or caused to flow into an amine at a temperature of 0° to 60° C., preferably at a temperature of 10° to 20° C., whereby the 2-chloronicotinic acid chloride ammonolyzes to 2-chloronicotinic acid amide and precipitates out in a crystalline form. Aqueous ammonia in a concentration of 10 to 25 percent, preferably 22 to 25 percent, can be used as the amine. The amine can be, for example, an aliphatic amine, preferably methylamine, dimethylamine or diethylamine, in an aqueous solution.

The process of this invention permits the conversion of 2-chloronicotinic acid chloride, which has been produced by a known method, in a simple and easy manner into 2 chloronicotinic acid amide.

Whenever 2-chloronicotinic acid has been made using phosphorus oxychloride, for example, according to the process of East German Pat. No. 80,209, the phosphorus oxychloride (at 35° C and at 50 torr) and subsequently the 2-chloronicotinic acid chloride (at 110° to 120° C and at 10 torr) are distilled off under vacuum. The distilled 2-chloronicotinic acid chloride is allowed subsequently to flow into aqueous, concentrated ammonia at a temperature of 0° to 60° C., preferably at 10° to 20° C. The 2-chloronicotinic acid chloride can also be used dissolved in a solvent, for example, dioxane, benzol, ethylacetate, methylenechloride, toluene, etc. - at the same time the 2-chloronicotinic acid chloride is ammonolyzed. After cooling, pure amide precipitates in crystaline form.

In order to remove any 6-chloronicotinic acid amide, developed possibly as a by-product, the 2-chloronicotinic acid amide is recrystallized from an alcohol having 1 to 6 carbon atoms, preferably ethanol.

As used herein, all parts, ratios, percentages and proportions are on a weight basis unless otherwise stated or otherwise obvious to one ordinarily skilled in the art.

EXAMPLE 1

70 g, of nicotinic acid-N-oxide were suspended in 300 ml of $POCl_3$. Then 51.5 gm. of triethylamine were added drop by drop at ambient temperature, the rate being such that the reaction temperature did not exceed 60° C. Then the solution was heated for another 3 hours to 110° C. Subsequently, phosphorus oxychloride was distilled off at 50 torr and the 2-chloronicotinic acid chloride was distilled off at 10 to 12 torr. The distilled 2-chloronicotinic acid chloride was allowed to flow into 400 ml of aqueous concentrated ammonia (24 percent) whereby it was ammonolyzed. The ammonolysis temperature was maintained at 10° C. The precipitated 2-chloronicotinic acid amide was sucked off and washed with water. The product yield was 45 to 50 percent, related to the starting nicotinic acid-N-oxide. The crude amide was recrystallized from ethanol for the removal of any 6-chloronicotinic acid amide. The 2-chloronicotinic acid had a melting point of 164° to 165° C. The net yield of 2-chloronicotinic acid was 35 to 40 percent.

EXAMPLE 2

Example 1 was repeated, except that the predistilled acid chloride was dissolved in about 150 ml of dioxane and ammonolyzed in 400ml of aqueous ammonia (24 percent). The net yield was 38 to 43 percent, related to nicotinic acid-N-oxide. The gross yield was 48 to 53 percent.

EXAMPLE 3

Example 1 was repeated, except that benzol was used instead of dioxane. The net yield was 48 to 53 percent. The gross yield was 60 to 65 percent.

EXAMPLE 4

Example 1 was repeated, except that ethylacetate was used instead of dioxane. The net yield was 40 to 45 percent. The gross yield was 50 to 55 percent.

EXAMPLE 5

Example 1 was repeated, except that methylene chloride was used instead of dioxane. The net yield was 45 to 50 percent. The gross yield was 55 to 60 percent.

EXAMPLE 6

Example 1 was repeated, except that toluene was used instead of dioxane. The net yield was 50 to 55 percent. The gross yield was 63 to 68 percent.

What is claimed is:

1. The process for the production of 2-chloronicotinic acid amide from nicotinic acid-N-oxide, characterized in that 2-chloronicotinic acid chloride is distilled off from the nicotinic acid-N-oxide reaction product and the distilled 2-chloronicotinic acid chloride is allowed to flow into an amide at a temperature of 0° to 60° C., whereby the 2-chloronicotinic acid chloride is ammonolyzed to 2-chloronicotinic acid amide and precipitates in a crystalline form.

2. The process as claimed in claim 1 wherein the 2-chloronicotinic acid amide is recrystallized from an alcohol having 1 to 6 carbon atoms.

3. The process as claimed in claim 1 wherein said amine is an aqueous ammonia solution having a concentration of 10 to 25 percent of ammonia.

4. The process as claimed in claim 3 wherein the water is at a temperature between 10° and 20° C.

5. The process as claimed in claim 3 wherein said aqueous ammonia solution has a concentration of 22 to 24 percent of ammonia.

6. The process as claimed in claim 1 wherein said amine is an aqueous solution of an aliphatic amine.

7. The process as claimed in claim 6 wherein the water is at a temperature between 10° and 20° C.

8. The process as claimed in claim 6 wherein said aliphatic amine is methylamine, dimethyl amine or diethylamine.

* * * * *